United States Patent [19]

Smith

[11] Patent Number: 5,945,579

[45] Date of Patent: Aug. 31, 1999

[54] MODIFICATION OF CROP PLANT ARCHITECTURE TO ENHANCE YIELD BY CAUSING PROXIMITY-CONDITIONAL DWARFING TO CONTROL SHADE AVOIDANCE REACTIONS

[75] Inventor: Harry Smith, Loughborough, United Kingdom

[73] Assignee: The University of Leicester, Leicester, United Kingdom

[21] Appl. No.: 08/539,652

[22] Filed: Oct. 5, 1995

[51] Int. Cl.$^6$ .............................. A01H 5/00; A01H 5/10; C12N 5/14; C12N 15/29

[52] U.S. Cl. ...................... 800/298; 435/320.1; 435/419; 435/468; 536/23.6; 800/278; 800/305; 800/306; 800/307; 800/309; 800/310; 800/312; 800/313; 800/315; 800/316; 800/317; 800/317.2; 800/317.3; 800/317.4; 800/318; 800/320; 800/320.1; 800/320.2; 800/320.3; 800/322; 800/323; 800/323.1; 800/323.2; 800/323.3

[58] Field of Search ..................................... 800/205, 250, 800/23.6, DIG. 58, DIG. 56, DIG. 55, DIG. 57, DIG. 23, DIG. 25, DIG. 26, DIG. 17, DIG. 14, DIG. 9, DIG. 42, DIG. 45, DIG. 60, DIG. 15, DIG. 13, DIG. 44, DIG. 40, DIG. 18, DIG. 19, DIG. 21, DIG. 64, DIG. 65, DIG. 38, DIG. 39, DIG. 11, DIG. 12, DIG. 10; 536/23.6; 435/172.3, 3, 419, 320.1, 69.1

[56] References Cited

PUBLICATIONS

Chory J, et al. "From seed germination to flowering, light controls plant development via a pigment phytochrome." PNAS 93: 12066–12071 1996.

Smith, "Plant Molecular Biology Biotechnology and Environment", Program and Abstracts, 22nd Aharon Katzir––Katchalsky Conference, (1994).

McCormac, Light–Grown Plants of Trang. Tobacco Express. Intro. Oat Phytochrm. A Gene Under the Control of A Const. Viral Promoter Exhibit Persis. Growth Inhib. by Far–Red Lght. Planta. vol. 188, pp. 173–181, (1992).

Whitelam et al., "Action & Function of PhytoChrome Family Members Revealed Through Study of Mutant & Transgenic Plants", Plant, Cell & Environ., vol. 17, pp. 615–625, (1994).

Smith, "Physiological and Ecological Function Within The Phytochrome Family", Annu. Rev. Plant Physiol. Mol. Biol., vol. 46, pp. 289–315, (1995).

Smith, "The Ecological Function of the Phytochrome Family Clues To A Transgenic Programme of Crop Improvement", Photochemistry & Photobiology, vol. 56, No. 5, pp. 815–822, (1992).

Schmitt et al., "Light Spectral Quality Phytochrome and Plant Competition", Tree, vol. 8, No. 2, pp. 47–51, (1993).

Smith, "Phytochrome Transgenics: Functional, Ecological and Biotechnological Applications", Seminars in Cell Biology, vol. 5, pp. 315–325, (1994).

McCormac, "Photoregulation By the Phytochrome Family: A Physiological Study of Transgenic Plants", Thesis Submitted for Doctor of Philosophy, University of Leicester, pp. 1–212, (1993).

Cherry et al., "Characterization of Tobacco Expressing Functional Oat Phytochrome", Plant Physiol, vol. 96, pp. 775–785, (1991).

Quail et al., "Phytochromes:Photosensory Perception and Signal Transduction", Science, vol. 268, pp. 675–680, (1995).

Whitelam et al., "Phytochrome A Null Mutants of Arabidopsis Display a Wild–Type Phenotype in White Light", The Plant Cell, vol. 5, pp. 757–768, (1993).

Stockhaus et al., "Serine–to–Alanine Substitutions at the Amino–Terminal Region of Phytochrome A Result in an Increase in Biological Activity", Genes & Devel., vol. 6., pp. 2364–2372, (1992).

Smith et al., "Phytochrome, a Family of Photoreceptors With Multiple Physiological Roles", Plant, Cell and Environ., vol. 13, pp. 695–707, (1990).

Quail, "Phytochrome Genes and Their Expression", Photomorphogenesis in Plants—2nd Edition pp. 71–104, (1994).

Boylan et al., "Dominant Negative Suppression of Arabidopisis Photoresponses y Mutant Phytochrome A Seque, Identifies Spatially Discrete Reg. Domains in Photoreceptor", The Plant Cell, vol. 6, pp. 449–460, (1994).

Boylan et al., "Oat Phytochrome is Biologically Active in Transgenic Tomatoes", The Plant Cell, vol. 1, pp. 765–773, (1989).

McCormac et al., "Photoresponses of Transgenic Arabidopsis Seedlings Expressing Introduced Phytochrome B–Encoding cDNAs", The Plant Journal, vol. 4, No. 1, pp. 19–27, (1993).

McCormac et al., "Photoresponses of Transgenic Tobacco Plants Expressing an Oat Phytochrome Gene", Planta, vol. 185, pp. 162–170, (1991).

Keller et al., "Expression of a Functional Monocotyledonous Phytochrome in Transgenic Tobacco", pp. 1005–1012.

*Primary Examiner*—Douglas W. Robinson
*Assistant Examiner*—Amy J. Nelson
*Attorney, Agent, or Firm*—Foley & Lardner

[57] ABSTRACT

Provided are trnasgenic plants comprising cells transformed or transfected with a recombinant DNA construct containing a coding sequence which encodes phytochrome A, which when expressed, causes the stimulation of phytochrome A and confers upon said plant the ability to undergo proximity-conctitional dwarfing Also provided are a recombinant DNA construct containing a coding sequence encoding phytochrome A, which when expressed, is effective in conferring the trait of proximity-conditional dwarfing on plants comprising cells transformed ar tansfected with this construct, a method for conferring proximity-conditional dwarfing upon plants, transgenic plants produced by this method, and seeds obtained by growing such plants.

12 Claims, 4 Drawing Sheets

MODIFICATION OF CROP PLANT ARCHITECTURE TO ENHANCE YIELD BY CAUSING PROXIMITY-CONDITIONAL DWARFING TO CONTROL SHADE AVOIDANCE REACTIONS

BACKGROUND OF THE INVENTION

1. Field of the Invention

The present invention relates to the field of plant improvement via genetic engineering. More particularly, the present invention relates to the modification of plant growth and structure by molecular biological means to enhance the yield, in particular the yield of harvestable components, of agronomic and horticultural crop plants grown in the field. This is achieved by providing transgenic plants in which shade avoidance reactions, which normally occur in dense crop stands, and which are mediated by the phytochrome system, are controlled. In this way, wasteful redirection of assimilates to stem growth, production of elongated plants susceptible to lodging, and reduction of harvest index can, in turn, be controlled, thereby providing plants with improved performance characteristics.

2. Description of Related Art

Phytochrome A (which is encoded by PHYA; see below) accumulates in etiolated wild-type (WT) seedlings to high levels, where it mediates stem growth inhibition in response to light, the wavelength maximum being in the far-red (FR=700–800 nm region of the photospectrum). Phytochrome B (which is encoded by PHYB; see below) acts principally in light-grown plants, where it modulates stem growth as a function of the relative amounts of red (R=600–700 nm) and FR radiation. When the proportion of FR is high, as in plant canopies, phytochrome B induces the shade avoidance syndrome, involving marked increases in stem extension and concomitant decreases in the growth of other organs, e.g. harvestable components such as leaf, fruit and storage organs. Normally, phytochrome A is not active in light-grown plants as it is rapidly degraded and its synthesis down-regulated in plants exposed to light (Quail, P. H., 1994, In Photomorphogenesis in Plants, R. E. Kendrick and G. H. M. Kronenberg, Eds., Second Edition, Kluwer Academic Publishers, Dordrecht, pps. 71–104). Transgenic plants expressing introduced PHYA cDNAs at high levels are severely dwarfed (McCormac, A. C. et al., 1992, Planta, 188: 173–181; Cherry, J. R. et al., 1991, Plant Physiol., 96: 775–785).

Shade avoidance is a mechanism whereby, in an attempt to out-compete their neighbors, plants grown in close proximity respond to far-red (FR) radiation reflected from the leaves of neighboring plants by increasing significantly their stem length at the expense of leaf, fruit and storage organ development, thereby adversely affecting the yield of harvestable components (Smith, H., 1982, Ann. Rev. Pl. Physiol., 33: 481–518; Schmitt, J. M. and Wulff, R. D., Trends in Ecology and Evolution, 8: 47–51; Ballare, C. L. et al., 1990, Science, 247: 329–332; Smith, H., 1995, Ann. Dev. Pl. Physiol. Mol. Biol., 46: 289–315; Schmitt, J. M. et al., 1995, American Naturalist, 146: 937–953).

This proximity perception and response is mediated primarily by phytochrome B (Smith, H. and Whitelam, G. C., 1990, Plant Cell Environ., 13: 696–707; Whitelam, G. C. and Harberd, N. P., 1994, Plant Cell Environ., 17: 615–625), which is encoded by the PHYB gene, a member of the small, diverse PHY multigene family (Sharrock, R. A. and Quail, P. H., 1989, Genes Devel., 3: 534–544); phytochrome D may also be involved in shade avoidance responses (Robson, P. H. R. and Smith, H. unpublished data). Phytochrome A (which is encoded by the PHYA gene) is not normally involved in shade avoidance (Whitelam, G. C. et al., 1993, Plant Cell, 5: 757–768), but when overexpressed in transgenic plants can antagonise the action of phytochrome B (McCormac, A. C. et al., 1992, supra; Smith, H., 1994, Seminars in Cell Biology, 5: 315–325). Experiments performed to date (McCormac, A. C. et al., 1992, supra), have only shown that transgenic plants expressing introduced PHYA cDNA at high levels are severely dwarfed, irrespective of the proximity of neighboring plants.

SUMMARY OF THE INVENTION

U.S. Pat. No. 5,268,526 to Hershey et al. entitled "Overexpression of Phytochrome in Transgenic Plants" discloses transgenic overexpression of a phytochrome construct to effect changes in a number of agronomically useful characteristics in plants. Among other changes, constitutive semi-dwarfing of transgenic plants is disclosed.

In contrast, and as will be described in detail below, the present invention provides transgenic plants expressing a phytochrome A coding sequence (or biologically active fragment or analogue thereof) which exhibit substantially the same growth pattern and plant architecture as wild-type non-transgenic plants when grown in isolation, but which exhibit proximity-conditional dwarfing, i.e. dwarfing that is not constitutive and which only results when the plants are grown in close proximity to neighboring plants. The invention described herein thus differs from that of Hershey et al., who neither disclose nor suggest proximity-conditional dwarfed transgenic plants, and provides the benefit of permitting planting of crop plants at increased densities without the disadvantages of reduced yield normally associated with such planting, or with planting at standard densities without the disadvantage of uncontrolled shade avoidance reactions that cause the allocation of resources into wasteful plant components. Unlike the constitutive semi-dwarf plants of Hershey et al., the transgenic plants of the present invention exhibit adaptable phenotypic changes depending upon plant density. Without being bound to any particular mechanistic explanation of the present invention, one can hypothesize that the methods described herein produce transgenic plants in which the amount or activity of phytochrome A or fragments or analogues thereof are present in a range of levels that confer proximity-conditional dwarfing rather than constitutive semidwarfing on plants.

The present inventor has surprisingly found that, despite the teachings of the prior art, plants expressing introduced PHYA cDNA at moderate levels, rather than being constitutively dwarfed as would be expected, are in fact subject to proximity-conditional dwarfing. In a controlled-release field experiment as described below, the response to crowding of transgenic tobacco plants expressing at a moderate level an introduced oat PHYA cDNA was tested It was discovered that at low planting densities, the architecture of the transgenic plants was similar to that of control wild-type plants; in crowded stands, i.e. at high planting densities, the transgenic plants allocated fewer assimilates to stem extension, resulting in proximity-conditional dwarfing and the allocation of more assimilates to harvestable components.

These results demonstrate that the transgenic suppression of shade avoidance permits crop plant architecture to be modified conditionally upon density. Furthermore, these results indicate that transgenic plants can be generated which are capable of growing at high densities, yet which waste fewer resources on stem growth for example, and instead allocating these resources to the development of harvestable components, allowing for increased farming efficiency.

Accordingly, it is an object of the present invention to provide transgenic plants comprising cells transformed or transfected with a recombinant DNA construct containing a coding sequence which encodes phytochrome A, which when expressed, causes the stimulation of phytochrome A and confers upon said plants the ability to undergo proximity-conditional dwarfing.

It is a second object of the present invention to provide recombinant DNA constructs containing a coding sequence which encodes phytochrome A which, when expressed, is effective in conferring the trait of proximity-conditional dwarfing on plants comprising cells transformed or transfected with this construct.

Further objects of the present invention include providing a method for conferring proximity-conditional dwarfing upon plants, transgenic plants produced by this method, and seeds obtained by growing such plants.

The further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only and are not limitative of the present invention, in which.

DETAILED DESCRIPTION OF THE PREFERRED EMBODIMENTS

Figure 1:
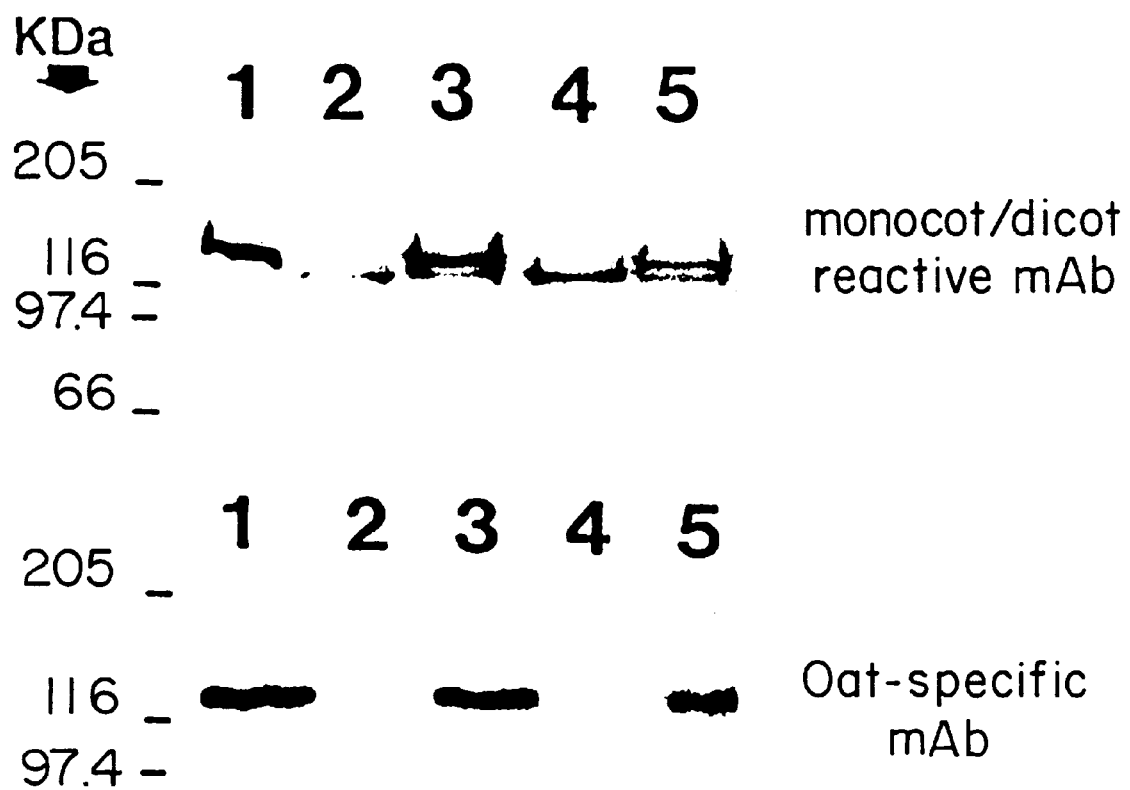
FIG. 1 is a Western blot showing the expression of an oat PHYA cDNA in transgenic tobacco. Transgenic lines were generated by Agrobacterium-mediated transformation of tobacco using an oat PHYA CDNA fused to the Camv 35S (Cauliflower Mosaic Virus 35S; see below) promoter and selected via kanamycin resistance, as described in Example 2. Three antibiotic-resistant lines were selfed, and progeny were tested for phytochrome A production. Protein extracts of etiolated seedlings of oat (lane 1), WT tobacco (lane 2), and transgenic tobacco lines Y12 (lane 3), Y5 (lane 4) and Y10 (lane 5), were separated on an 8% SDS-polyacrylamide gel, blotted onto a nitrocellulose membrane, and the resulting blots probed with a monoclonal antibody specific for phytochrome from monocotyledonous plants, and a monoclonal antibody reactive with phytochromes from either monocotyledonous or dicotyledonous plants (Holdsworth, M. L. and Whitelam, G. C., 1987, Planta, 172: 539–547). An oat specific band of the correct molecular mass is present in transgenic lines Y10 (lane 5) and Y12 (lane 3), but absent from WT tobacco (lane 2) and from transgenic line Y5 (lane 4), which was kanamycin-resistant but did not express the introduced PHYA cDNA. Each of lanes 1–5 displays reactivity to the monoclonal antibody reactive with phytochromes from either monocotyledonous or dicotyledonous plants.

The following detailed description of the invention is provided to aid those skilled in the art in practicing the present invention. Even so, the following detailed description of the invention should not be construed to unduly limit the present invention as modifications and variations in the embodiments discussed herein may be made by those of ordinary skill in the art without departing from the spirit or scope of the present invention.

The contents of each of the references discussed herein, including the references cited therein, are herein incorporated by reference in their entirety.

The present invention provides monocotyledonous or dicotyledonous plants that exhibit proximity-conditional dwarfing, in particular transgenic monocotyledonous or dicotyledonous plants comprising cells transformed or transfected with a recombinant DNA construct comprising a DNA coding sequence operably linked to at least one regulatory expression signal which functions in plants, wherein said DNA coding sequence is expressed, causing phytochrome A to be stimulated and conferring upon said plant the ability to undergo proximity-conditional dwarfing.

Definitions

"Stimulation" means (1) that the amount of phytochrome A is affected so that this amount is increased compared to that in wild-type, light-grown plant cells; or (2) that the normal biological activity of phytochrome A is affected so that its activity is enhanced compared to that in wild-type, light-grown plant cells; or (3) that a functional fragment or analogue of phytochrome A is caused to be present in an amount, or to exhibit biological activity, greater than that of phytochrome A in normal, wild-type, light-grown plant cells.

Said fragments and analogues can comprise at least that part of phytochrome A that is required to effect proximity-conditional dwarfing. Said fragment or analogue can have the same, similar or greater activity as compared to phytochrome A in effecting proximity-conditional dwarfing. Fragments or analogues of phytochrome A useful in the present invention preferably exhibit between about −20% and about +450% of the activity of naturally occurring phytochrome A in effecting proximity-conditional dwarfing.

Said fragments and analogues include, for example, chimeric proteins, related proteins and mimotopes of phytochrome A.

For example, the construct can encode phytochrome A (Quail, 1994, supra), or a fragment thereof (Cherry, J. R., et al., 1992, Proc. Natl. Acad. Sci., USA, 89: 5039–5043; Cherry, J. R., 1993, Plant Cell, 5: 565–575), or an analogue thereof (Stockhaus, J. et al., 1992, Genes & Development, 6: 2364–2372; Boylan, M. T. et al., 1994, Plant Cell, 6: 449–460). Analogues include a chimeric construct of a fragment of phytochrome A and one or more fragment(s) of phytochrome A, or phytochrome B, or another phytochrome (Quail, P. H. et al., 1995, Science, 268: 675–680), or a phytochrome related to phytochrome A. from a non-angiospennous plant (Okamoto, H. et al., 1993, Plant and Cell Physiology, 8: 1329–1334), wherein such fragment, analogue, chimeric protein, related protein or mimotope has at least the same or similar activity as phytochrome A in effecting proximity-conditional dwarfing. The construct can encode an analogue of phytochrome A having a longer half-life than phytochrome A, for example having less affinity for a receptor site on an enzyme which degrades phytochrome A.

Said fragment or analogue having a longer half-life than phytochrome A (McCormac et al., 1992, supra) causes its amount to be higher in the light-grown transgenic plant than in the wild-type plant. Alternatively, said fragment or analogue can have altered biological properties, such as enhanced activity in response to FR radiation (Stockhaus et al., 1992, supra) such that low amounts of the introduced fragment or analogue will result in greater phytochrome A activity in the transgenic light-grown plant than in the wild-type plants.

Alternatively, for example, the construct can encode a mimotope (Geysen, H. M. et al., 1987, Journal of Immunological Methods, 102: 259–274) made to a fragment of phytochrome A which is bound by an enzyme which degrades phytochrome A. Such a mimotope can bind to the phytochrome A receptor site of the enzyme, competitively inhibiting the binding of phytochrome A to the enzyme and thereby inhibiting its degradation.

Alternatively, for example, the construct can encode a molecule required for transcription of the PHYA gene, or it can encode a molecule which affects the half-life of the PHYA MRNA or which affects the rate of translation of the PHYA MRNA.

Such fragments and analogues may be employed using conventional genetic engineering procedures and may be used according to the examples given herein and by other methods which will be readily apparent to one skilled in the art.

"Proximity-conditional dwarfing" refers to the reduction, suppression or elimination of normal shade avoidance responses such that, when the modified plants are grown in close proximity to neighbors of the same, or other, species, the phytochrome-B-mediated, or phytochrome-D-mediated, enhancement of stem, petiole and leaf elongation responses are not observed, resulting in a changed growth pattern and plant architecture in which the modified plants are less-elongated than the wild-type plants grown under similar conditions; whereas, when the modified plants are grown in isolation from neighbors, their growth pattern and architecture are similar to that of wild-type plants.

Proximity-conditional dwarfing useful in enhancing crop yield can be achieved by stimulating phytochrome A in the range of from about 1.5 to about 4.5 times, preferably from about 2.0 to about 3.5 times, and more preferably from about 2.5 to about 3.0 times in etiolated cells of plants of the present invention, compared to phytochrome A in etiolated wild-type plant cells.

For example, phytochrome A can be found at a nominal level of 100 units in cells of wild-type etiolated plants, whilst in the transformed or transfected etiolated cells of the present invention, phytochrome A can be found at a level of 250 units. This example shows phytochrome A being stimulated by 2.5 times in etiolated transformed or transfected cells, compared to phytochrome A in etiolated wild-type plant cells. Note that only etiolated cells or plants are referred to as phytochrome A is readily degraded in plants or cells subject to white light (Quail, P. H., 1993, supra)

As shown by way of the non-limiting Examples presented below, constructs useful in the present invention may stimulate only phytochrome A. (Of course, useful constructs can also encode a fragment or analogue of phytochrome A, as discussed supra). Such constructs may comprise at least a PHYA gene or a PHYA-encoding cDNA, or a fragment or analogue thereof exhibiting phytochrome A activity which is capable of effecting proximity-conditional dwarfing, and a promoter therefor. In the Examples presented below, oat PHYA cDNA has been employed. Other PHYA genes and cDNAs are known in the art, and can be used in the method of the present invention (Quail, P. H., 1994, supra; Sharrock, R. A. and Quail, P. H., 1989, supra; McCortnac, A. C. et al., 1992, supra)

Due to the interactions between the various members of the phytochrome families, it is possible for the exact nature and extent of the proximity-conditional dwarfing of the present invention to be moderated by altering the activity of phytochrome A and other phytochromes such that, for example, the intemodal length in plants grown at low planting densities and those grown at high planting densities more closely approximate one-another.

Promoters

Promoters useful in the present invention preferably possess one or more of the following properties: constitutive expression of inserted sequences throughout the plant; intermediate rate of expression of inserted sequences; organ-specific expression in stems and/or petioles and/or leaf sheathes; cell-specific expression in vascular tissues. These properties are defined as to drive expression of the inserted sequence(s) at a level that results in phytochrome A stimulation to produce proximity-conditional dwarfing when the modified plants are grown at planting densities in the field that are standard for the particular crop plant, or are more dense than standard for that crop plant.

Examples of promoters useful in the present invention include, inter alia, the cauliflower mosaic virus 35S (CaMV 35S) promoter, the maize polyubiquitin (ub 1) promoter (Christensen, A. H. et al., 1992, Plant Mol. Biol. 18: 675–689), the *Asparagus officinalis* pathogenesis-related vascular-tissue-specific (AOPRI) promoter (Warner, S. A. J.

et al., 1994, Plant Journal, 6: 31–43) the rice ribulose-bisphosphate carboxylase (rbcs) promoter (Kyozuka, J. et al., Plant Physiology, 102: 991–1000), the maize shrunken-1 promoter (Maas, C. et al., Plant Mol. Biol., 16: 199–207), and the *Arabidopsis thaliana* phytochrome B promoter (Wester, L. et al., 1994, Plant Journal, 5: 261–272).

Plant Cells and Plants

Plants useful in the present invention include those of both monocotyledonous and dicotyledonous species, for example agronomic crop plants, horticultural crop plants, and ornamental plants. Agronomic or horticultural crop plants include cereals, non-cereal seed crops, root crops, vegetable crops, horticultural crops, and fruit crops. Cereal crops include wheat, rye, barley, oats, maize, buckwheat, sorghum, and rice. Non-cereal seed crops include peas, beans, soybeans, oil-seed rape, canola, linseed, sunflower, and flax. Root crops include potato, sweet potato, sugar beet, carrot, swede, and turnip. Vegetable crops include asparagus, mustard, lettuce, tobacco, and cauliflower. Horticultural crops include tomato, egg plant, cucumber, celery, melon, and squash. Fruit crops include strawberry, blackberry, blueberry, apple, apricot, peach, pear, plum, orange, cranberry, and lemon. Other crop plants include cotton and sugarcane. Ornamental plants include petunia, chrysanthemum, carnation, poinsettia, begonia, tradescantia, and snapdragon.

Plant Transformation and Transfection

The disclosure herein identifies cDNAs and other nucleic acids that are able to confer proximity-conditional dwarfing onto plants. Plants can be made to express the proximity-conditional dwarfing phenotype by introducing these cDNAs and nucleic acids therein in a functionally operable manner so that they are expressed at levels effective in causing proximity-conditional dwarfing under field conditions, thereby improving plant performance and crop yield.

Transgenic plants that exhibit proximity-conditional dwarfing as discussed herein can be produced by:

(a) transforming plant cells with a DNA molecule comprising operatively linked in sequence in the 5' to 3' direction:
   (i) a promoter region that directs the transcription of a gene in plants;
   (ii) a structural DNA sequence that encodes an RNA sequence which encodes a peptide, polypeptide, or protein effective in stimulating phytochrome A and conferring the ability to undergo proximity-conditional dwarfing in a plant comprising said cells; and
   (iii) a 3' non-translated region which encodes a polyadenylation signal which functions in plant cells to cause transcriptional termination and the addition of polyadenylate nucleotides to the 3' end of said RNA sequence;

(b) selecting plant cells that have been transformed;

(c) regenerating plant cells that have been transformed to produce differentiated plants; and (d) selecting a transformed plant which expresses said structural DNA sequence and which undergoes proximity-conditional dwarfing.

The 3' non-translated region can be the 3' polyadenylation signal from the CAMV 35S transcript.

Monocot Transformation

Methods for producing transgenic plants in a variety of different monocots are currently available, and these methods are equally applicable to the present invention. Successful transformation and plant regeneration have been achieved in asparagus (*Asparagus officinalis;* Bytebier et al., 1987, Proc. Natl. Acad. Sci. USA 84: 5345); barley (*Hordeum vulgarae;* Wan and Lemaux, 1994, Plant Physiol. 104: 37); maize (*Zea mays;* Rhodes et al., 1988, Science 240: 204; Gordon-Kamm et al., 1990, Plant Cell 2: 603; Fromm et al., 1990, Bio/Technology 8: 833; Koziel et al., 1993, Bio/Technology 11: 194); oats (*Avena sativa;* Somers et al., 1992, Bio/Technology 10: 1589); orchardgrass (*Dactylis glomerata;* Hom et al., 1988, Plant Cell Rep. 7: 469); rice (*Oryza sativa,* including *indica* and *japonica* varieties; Toriyama et al., 1988, Bio/Technology 6: 10; Zhang et al., 1988, Plant Cell Rep. 7: 379; Luo and Wu, 1988, Plant Mol. Biol. Rep. 6: 165; Zhang and Wu, 1988, Theor. Appl. Genet. 76: 835; Christou et al., 1991, Bio/Technology 9: 957); rye (*Secale cereale;* De la Pena et al., 1987, Nature 325: 274); sorghum (*Sorghum bicolor;* Cassas et al., 1993, Proc. Natl. Acad. Sci. USA 90: 11212); sugar cane (Saccharum spp.; Bower and Birch, 1992, Plant J. 2: 409); tall fescue (*Festuca arundinacea;* Wang et al., 1992, Bio/Technology 10: 691); turfgrass (*Agrostis palustris;* Zhong et al., 1993, Plant Cell Rep. 13: 1); wheat (*Triticum aestivum;* Vasil et al., 1992, Bio/Technology 10: 667; Troy Weeks et al., 1993, Plant Physiol. 102: 1077; Becker et al., 1994, Plant J. 5: 299).

Dicot Transformation

Methods for transforming a wide variety of different dicots and obtaining transgenic plants are well documented in the literature (see Gasser and Fraley, 1989, Science 244: 1293; Fisk and Dandekar, 1993, Scientia Horticulturae, 55: 5–36; Christou, 1994, Agro Food Industry Hi Tech (March/April 1994) p. 17, and the references cited therein), and can also be applied in the present invention. A DNA encoding an RNA sequence which encodes a peptide, polypeptide, or protein effective in stimulating phytochrome A and conferring the ability to undergo proximity-conditional dwarfing in a plant comprising said cells discussed hereinbefore can be introduced into any of these dicotyledonous plants in order to produce transgenic plants that undergo proximity-conditional dwarfing in the field.

Transfection

Methods of plant cell transfection are widely known. Transfection of cells with a plasmid can be achieved, for example, using a particle gun, as follows:

(i) Preparation of DNA coated tungsten microprojectiles

Prepare a tungsten suspension by adding particles (M10: average diameter 10 $\mu$m) to absolute ethanol (50 mg per ml of ethanol) and store at −20° C. Wash particles with sterile distilled water and place 25 $\mu$l aliquots into microcentrifuge tubes. To each tube add 10 $\mu$g of plasmid DNA with 25 $\mu$l of a 1.0M solution of calcium chloride, and 10 $\mu$l of a 0.1M solution of spermidine (free base) and mix. Allow the suspension to stand for 10 minutes.

(ii) Particle bombardment

Having allowed the DNA-tungsten suspension to settle for 10 minutes, remove 25 $\mu$l of supernatant (which contains DNA-coated tungsten microparticles) from the suspension and place approximately 2 $\mu$l of the tungsten-DNA preparation onto the front surface of the macroprojectile. Place the macroprojectile into the barrel of the particle gun, with the DNA side facing down. Place a blank charge (Remington 1) into the barrel behind the macroprojectile and place the firing assembly over the barrel with the stopping plate in position. Place a leaf sample into the firing chamber and close the assembly. Switch on the vacuum pump until 275 mm Hg is reached and then fire the particle gun. Following bombardment, incubate the plates were incubated at 26° C. overnight.

Once transfection has taken place, plants may be regenerated as per Example 2 below.

The invention will now be further apparent from the following Examples, with reference to the accompanying figures, which demonstrate, in a non-limiting way, one form of proximity-conditional dwarfing.

EXAMPLE 1

Plasmid Construction

Plasmid construction was performed using plasmid pFY122, based on the pUC19 plasmid and containing a copy of the uninterrupted coding sequence of the oat-PHYA gene as a full length CDNA clone (Boylan, M. T. and Quail, P. H., 1989, Plant Cell, 1: 765–773). pFY122 was digested with EcoRl, releasing the 3' end of the phytochrome CDNA, and the end rendered blunt using the klenow fragment of DNA polymerase 1. The resulting DNA was cleaved with BamH1, and the 3.5 kbp fragment containing the full-length PHYA-CDNA was gel purified and subcloned into plasmid pROK2, which had been digested with BamHI and SmaI, to generate plasmid PRFY I. pROK2 is a binary system cloning vector based on pbin 19 (Bevan, M., 1984, Nucleic Acids Research, 12: 8711) and contains a polylinker flanked 5' by the promoter region and 3' by the downstream polyadenylation signals from the CAMV 35S transcript, a wide host range RK2 origin of replication, a bacterial selection marker, and a plant kanamycin-resistance coding sequence under the control of the CaMV 35S promoter and 3' sequences. In PRFY1 the complete phytochrome coding sequence was operably linked to the CaMV 35S promoter and 3' polyadenylation signals.

pRFY1 was mobilized from *Escherischia coli* strain XL1-blue into *Agrobacterium tumefaciens* strain 2260, using pRK2013 in *E. coli* strain HB101 for plasmid mobilization in a triparental conjugation. The Agrobacterium acceptor strain contained a chromosomally-located rifampicin resistance gene. Conjugates were selected, after 24 hours of growth at 28° C. on non-selective medium, by plating onto LB agar (10 g/l Tryptone, 5 g/l yeast extract, 5 g/l NaCl, 12 g/l agar) containing 100 $\mu$g/ml kanamycin, 100 $\mu$g/ml ampicillin, 200 $\mu$g/ml rifampicin. Restriction-enzyme digestion coupled with Southern blot analysis of total DNA from conjugate Agrobacterium colonies was used to check that the PHYA cDNA was maintained in the binary vector and also to confirm its orientation. Total DNA was extracted from a 2 day old culture of a kanamycin-resistant colony of Agrobacterium and digested with either Sac1 or Xba1. Fragments were separated on 0.8% agarose gel and blotted onto a nylon membrane (Hybond-N Amersham, U.K.). The resulting blot was probed with a full-length radiolabelled ($^{32}$P) cDNA probe (obtained as a 3.5 kbp fragment from EcoR1/BamH1 digestion of pFY122), and was washed under high stringency conditions: 0.5×SSC, 0.1% (w/v) sodium dodecyl sulphate (SDS) (20×SSC=3.0M NaCl, 0.3M NaCitrate pH 7.0). The pattern of restriction fragments which hybridized with the probe was compared with the restriction maps of the oat-PHYA-cDNA and the Agrobacterium vector. This showed the digestion pattern to be consistent with the cDNA having the correct orientation, with respect to the vector-linked promoter, for sense expression.

EXAMPLE 2

Plant Transformation

Constructs were mobilized into the plant genome via *Agrobacterium tumefaciens* infection of *N. tabacum* (cv. xanthi) leaf discs. Leaves of mature tobacco plants were surface sterilized in a 10% (v/v) solution of domestic bleach for 15 min. Cut leaf discs were soaked in a 1/50 dilution of an overnight culture of the Agrobacterium strain containing the oat-PHYA-cDNA vector (pRFYI). Infected leaf discs were placed onto plates of MSD4 X2 medium (MS salts supplemented with 30 g/l sucrose, 0.1 mg/l naphthaleneacetic acid, 1.0 mg/l 6-benzylaminopurine) and incubated under a low light intensity at 25° C. for 2 days. Subsequently, leaf pieces were transferred to fresh plates of MSD4 X2 containing 100 mg/l kanamcyin and 400 mg/l Augmentin, and were incubated further until shoot regeneration occurred. When shoots reached approximately 1 cm length they were excised and inserted into MS medium (supplemented with 30 g/l sucrose, 7 g/l agar) containing 110 mg/l kanamycin. Shoots in which root development was resistant to kanamycin were expressing at least the kanamycin-resistance gene part of the construct and had therefore been transformed. Stocks of each of the transformants were then grown, and progeny of selfed antibiotic-resistant lines tested for levels of phytochrome A production (FIG. 1) and used for further experiments (below). Transformants included strains Y5, Y10 and Y12.

EXAMPLE 3

Planting Out

Figure 3:
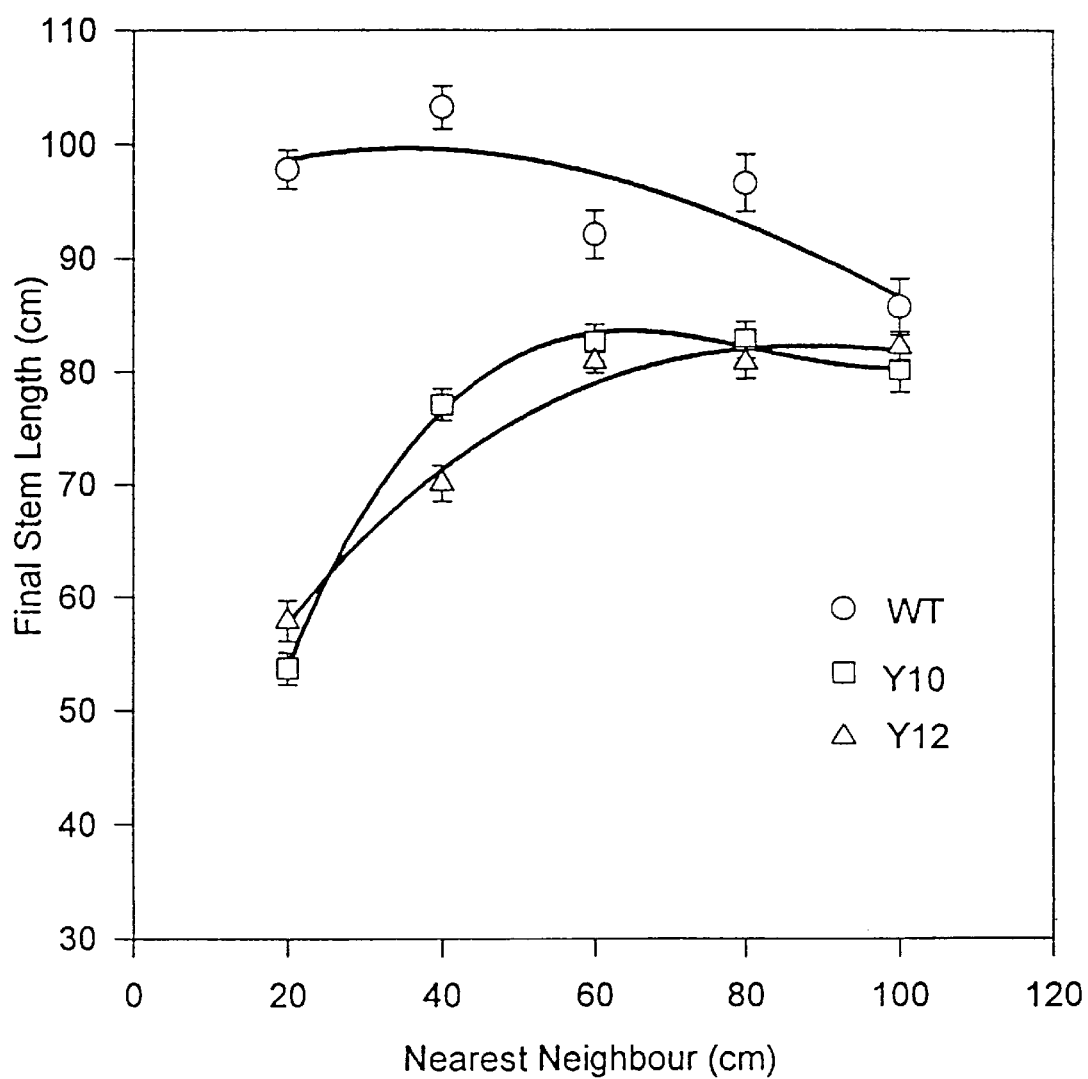
FIG. 3 shows the relationship between plant proximity and final height of WT and transgenic tobacco in the field. Seeds of WT and the Y10 and Y12 transgenic lines were sown and grown up in a contained green house, and seedlings transplanted to the field after 6 weeks (June). Three replicate plots of grids at 20, 40, 60, 80 and 100 cm planting distances were used for each line. Irrigation and herbicide treatments were applied as necessary. Plants were harvested after nine weeks growth, and total plant height recorded for 10 plants from the centre of each plot. The data represent means±standard error (n=30).
Figure 4:
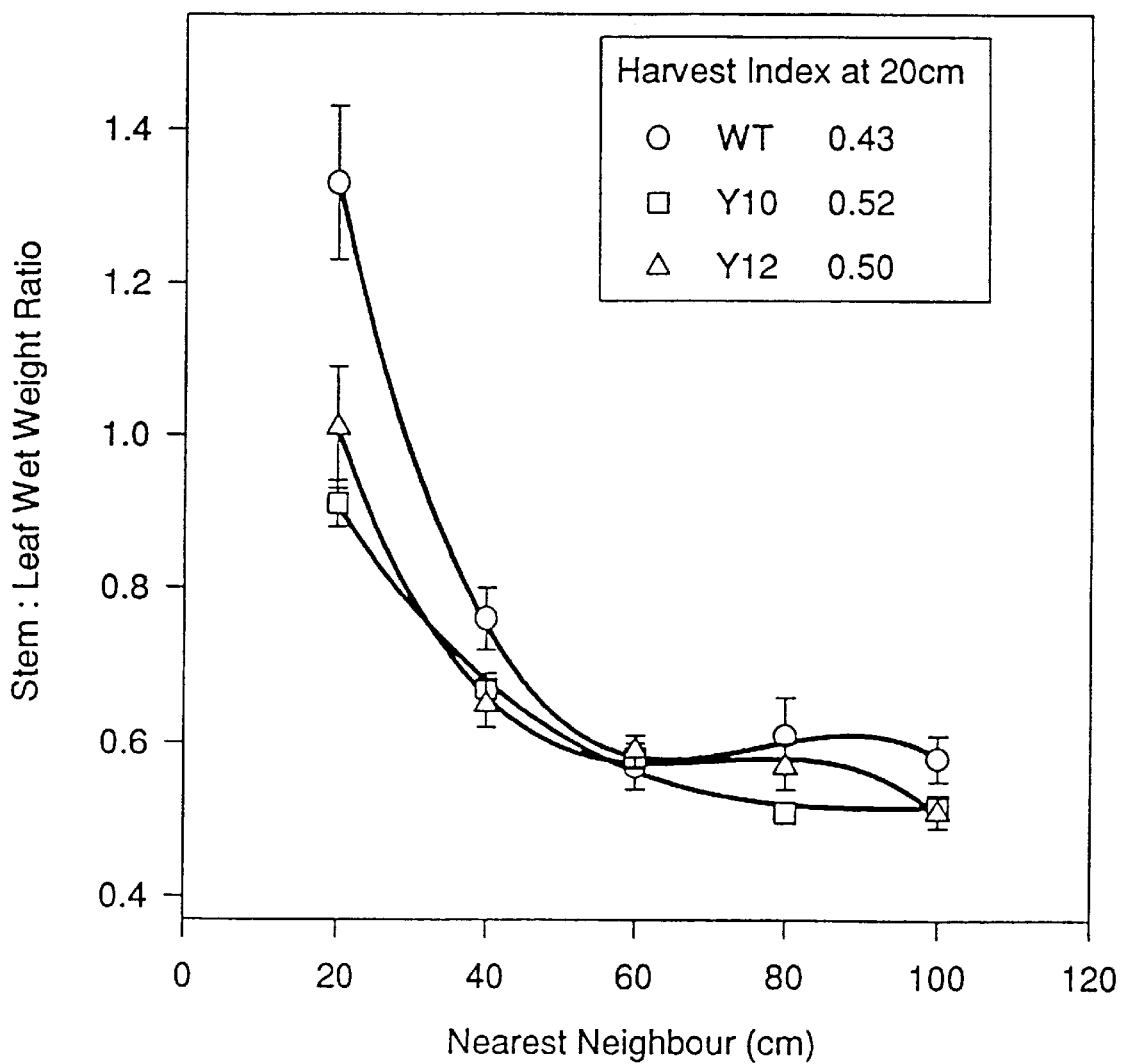
FIG. 4 shows the relationship between plant proximity and the ratio of stem:leaf biomass of WT and transgenic tobacco in the field. Final harvest data for total plant stem and leaf wet weight are expressed as a ratio to emphasize the partitioning of resources. Data are means±standard errors (n=30). Data for harvest index (i.e. weight of all leaves as a fraction of the total weight) at the densest planting are given in the inset.

WT, Y10 and Y12 plants were grown at five planting densities, replicated three times, in a controlled-release field experiment during the summer. FIG. 3 shows the final harvest data for total plant height, demonstrating the increased stem elongation of the WT plants as planting density increased. The Y10 and Y12 strains were indistinguishable from the WTs at the lowest planting density, but became substantially shorter as density increased, i.e. proximity-conditional dwarfing occurred. This proximity-conditional dwarfing is associated with a major change in the allocation of growth assimilates. At high planting densities total plant biomass was not significantly different between the three strains (WT, Y10, Y12), but allocation of biomass to stems and leaves was markedly altered by the heterologous phytochrome A. With increasing proximity of neighbors, WT plants allocated increasing proportions of assimilates to stems, and concomitantly less to leaves (FIG. 4). Proximity-related direction of assimilates to stem growth was significantly reduced in the transgenic PHY,4 expressers the heterologous phytochrome A appears to disable the shade avoidance responses mediated by the host plant's phytochrome B. Expressed as a harvest index (i.e., leaf biomass as a proportion of total biomass) these data indicate a 15% and 20% increase in Y 1 2 and Y I 0 respectively compared with the WT seedlings at high densities.

SUMMARY OF RESULTS

Figure 2:
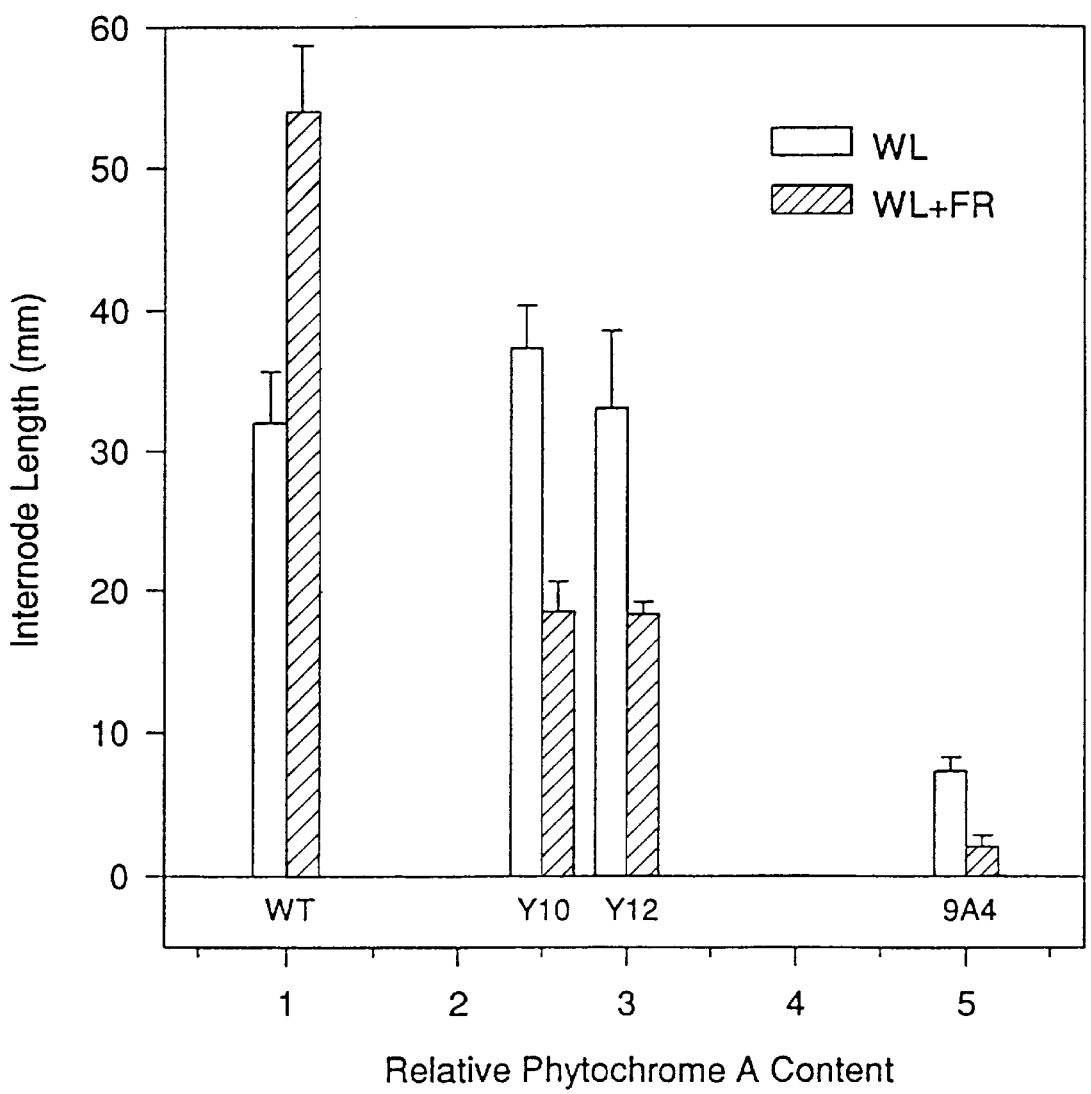
FIG. 2 shows the responses of WT and transgenic tobacco to additional far red light. Seedlings of WT and three transgenic lines (Y10, Y12, and 9A4) (see Cherry, J. R. et al., supra regarding 9A4) were grown in controlled environment cabinets at a temperature of 25±1° C. for four weeks (until the third true leaf had expanded) under continuous fluorescent white light lacking FR radiation (WL), and batches were then transferred for a further two weeks to identical conditions but under WL with additional high-irradiance FR (WL+FR). The WL fluence rate (400–700 nm) was 130 $\mu mol/m^2/s$, and that of the additional FR (700–800 nm) was 100 $\mu mol/M^2/s$. The lengths of the 9th internode were measured and plotted against the estimated relative levels of phytochrome A present in the four lines. The data represent means±standard efforts (n=10). The levels of phytochrome A in the Y10 and Y12 transgenic lines were estimated from densitometric scans of immunoblots such as those in FIG. 1, and for line 9A4 from information in Cherry, J. R. et al., 1991, supra.

Two lines (designated Y10 and Y12) of tobacco (*Nicotiana tabacum* cv. Xanthi) transformed with an oat PHYA cDNA driven by the CaMV 35S promoter were selected, in which the introduced gene was stably expressed at moderate levels. Levels of homologous and heterologous phytochrome A apoproteins were measured using specific monoclonal antibodies. Results (FIG. 2) indicate that etiolated Y10 and Y12 seedlings accumulated, respectively, about 2.5-fold and 3-fold the levels of phytochrome A of the etiolated WT plants (FIG. 1). Growth chamber tests were used to compare the low-level expressers with a high-level expresser (9A4) previously shown to accumulate about 5-fold WT levels of phytochrome A (Cherry, J. R. et al., 1991, supra). Internode growth of control WT seedlings in white light (lacking FR) was low and markedly increased by supplementation with FR (simulating canopy light environments) (FIG. 2), demonstrating a typical shade avoidance response. The 9A4 plants, on the other hand, were dwarfed in the white light and even more so in the FR-supplemented regime, a surprising result in itself and one not obtained by Cherry et al. Stem extension in Y10 and Y12, compared to WT plants, was unaffected in white light, but was inhibited under FR-supplementation, their internode lengths being intermediate between WT and 9A4, showing that the action of the heterologous phytochrome A is concentration-dependent. These data demonstrate antagonism between phytochromes A and B and suggest that, under field conditions, the Y10 and Y12 strains should be phenotypically normal when grown in isolation, but have modified architecture when grown in dense stands.

It is fully expected, as in the case of tobacco employed by way of example herein, that transgenic plants expressing the proximity-conditional dwarfing phenotype produced according to the methods of the present invention will stably and reproducibly transmit this trait to their progeny through their seeds.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

What is claimed is:

1. A method for conferring proximity conditional dwarfing on a monocotyledonous or dicotyledonous plant comprising the steps of:
    a. transforming cells of a monocotyledonous or dicotyledonous plant with a recombinant DNA construct comprising, operatively linked in sequence in the 5' to 3' direction:
        i. a plant compatible promoter;
        ii. a PHYA coding sequence; and
        iii. a 3' non-translated region encoding a polyadenylation signal functional in plant cells;
    b. selecting plant cells that have been transformed with said PHYA coding sequence;
    c. regenerating plant cells that have been transformed to produce transgenic plants that express the PHYA coding sequence; and
    d. selecting a PHYA-expressing transgenic plant that exhibits proximity conditional dwarfing as compared to a non-PHYA-transformed plant, wherein said PHYA-expressing transgenic plant has a harvest index at least 15% higher than the non-PHYA-transformed plant when grown at close proximity to neighbors of the same or other species.

2. The method according to claim 1, wherein said harvest index is at least 20%.

3. The method according to claim 1, wherein said PHYA coding sequence is an oat PHYA coding sequence.

4. The method according to claim 1, wherein said promoter comprises the CaMV 35S promoter.

5. The method according to claim 1, wherein said 3' non-translated region comprises a polyadenylation signal from the CaMV 35S transcript.

6. The method according to claim 1, wherein the increase in harvestable biomass as a proportion of total biomass is a result of the PHYA expression level in said transgenic plant grown at a high planting density.

7. The method according to claim 1, wherein said transgenic plant is selected from the group consisting of an agronomic crop, a horticultural crop, and an ornamental plant.

8. The method according to claim 1, wherein said transgenic plant is selected from the group consisting of a cereal crop, a non-cereal seed crop, a root crop, a vegetable crop, a horticultural crop, and a fruit crop.

9. The method according to claim 8, wherein
    said cereal crop is selected from the group consisting of wheat, rye, barley, oats, maize, buckwheat, sorghum, and rice;
    said non-cereal seed crop is selected from the group consisting of peas, beans, soybeans, oil-seed rape, canola, linseed, sunflower, and flax;
    said root crop is selected from the group consisting of potato, sweet potato, sugar beet, carrot, swede, and turnip;
    said vegetable crop is selected from the group consisting of asparagus, mustard, lettuce, tobacco, and cauliflower;
    said horticultural crop is selected from the group consisting of tomato, eggplant, cucumber, celery, melon, and squash; and
    said fruit crop is selected from the group consisting of strawberry, blackberry, blueberry, apple, apricot, peach, pear, plum, orange, cranberry, and lemon.

10. The method according to claim 7, wherein said transgenic plant is cotton or sugarcane.

11. The method according to claim 7, wherein said transgenic plant is selected from the group consisting of petunia, chrysanthemum, carnation, poinsettia, begonia, tradescantia, and snapdragon.

12. The method according to claim 8, wherein said transgenic plant is tobacco.

* * * * *